United States Patent
Harrer et al.

(10) Patent No.: US 10,596,377 B2
(45) Date of Patent: Mar. 24, 2020

(54) SEIZURE DETECTION, PREDICTION AND PREVENTION USING NEUROSTIMULATION TECHNOLOGY AND DEEP NEURAL NETWORK

(71) Applicant: International Business Machines Corporation, Armonk, NY (US)

(72) Inventors: Stefan Harrer, Hampton (AU); Filiz Isabell Kiral-Kornek, Collingwood (AU); Benjamin Scott Mashford, Malvern East (AU); Subhrajit Roy, Melbourne (AU); Susmita Saha, Melbourne (AU)

(73) Assignee: International Business Machines Corporation, Armonk, NY (US)

( * ) Notice: Subject to any disclaimer, the term of this patent is extended or adjusted under 35 U.S.C. 154(b) by 180 days.

(21) Appl. No.: 15/828,409

(22) Filed: Nov. 30, 2017

(65) Prior Publication Data
US 2019/0160287 A1    May 30, 2019

(51) Int. Cl.
*A61B 5/00*      (2006.01)
*A61N 1/36*     (2006.01)
(Continued)

(52) U.S. Cl.
CPC ........ *A61N 1/36064* (2013.01); *A61B 5/0476* (2013.01); *A61B 5/4094* (2013.01);
(Continued)

(58) Field of Classification Search
CPC ........... A61N 1/36064; A61N 1/36139; G16H 50/20; A61B 5/00476; A61B 5/4094;
(Continued)

(56) References Cited

U.S. PATENT DOCUMENTS

| | | |
|---|---|---|
| 6,480,743 B1 | 11/2002 | Kirkpatrick et al. |
| 7,006,872 B2 | 2/2006 | Gielen et al. |

(Continued)

OTHER PUBLICATIONS

S. Dumanis et al., "My Seizure Gauge Epilepsy Innovation Institute Workshop Notes," Epilepsy Foundation, Aug. 2017, p. 1-15, https://www.epilepsy.com/sites/core/files/atoms/files/Oct%2011%20Workshop%20Notes%20FINAL.pdf.

(Continued)

*Primary Examiner* — George Manuel
(74) *Attorney, Agent, or Firm* — Joseph Petrokaitis; Otterstedt, Wallace & Kammer, LLP (57) ABSTRACT

A method for neuromodulation includes monitoring brain activity of a patient using one or more electrodes attached to the patient, and using a first machine learning model to predict whether a patient will have a seizure based on the monitored brain activity of the patient. The method also includes, responsive to the first machine learning model predicting that the patient will have a seizure, using a second machine learning model to determine a neuromodulation signal pattern for preventing the predicted seizure. The method further includes using a neurostimulator to apply the determined neuromodulation signal pattern to the patient. The method also includes, after applying the determined neuromodulation signal pattern to the patient, detecting whether the patient had the predicted seizure based on the monitored brain activity of the patient. The method further includes adjusting at least the second machine learning model based on whether the patient had the predicted seizure.

20 Claims, 3 Drawing Sheets

(51) Int. Cl.
*G06N 3/04* (2006.01)
*G16H 50/20* (2018.01)
*A61B 5/0476* (2006.01)

(52) U.S. Cl.
CPC .......... *A61B 5/4836* (2013.01); *A61B 5/7267* (2013.01); *A61B 5/7275* (2013.01); *A61N 1/36139* (2013.01); *G06N 3/0454* (2013.01); *G16H 50/20* (2018.01); *A61B 2505/07* (2013.01)

(58) Field of Classification Search
CPC ... A61B 5/4836; A61B 5/7267; A61B 5/7275; A61B 2505/07; A61B 5/0476; G06N 3/0454
See application file for complete search history.

(56) References Cited

U.S. PATENT DOCUMENTS

| | | |
|---|---|---|
| 7,146,218 B2 | 12/2006 | Esteller et al. |
| 7,231,254 B2 | 6/2007 | DiLorenzo |
| 9,320,900 B2 | 4/2016 | DiLorenzo |
| 2004/0068199 A1 | 4/2004 | Echauz et al. |
| 2004/0267152 A1 | 12/2004 | Pineda |
| 2005/0107655 A1 | 5/2005 | Holzner |
| 2007/0067003 A1 | 3/2007 | Sanchez et al. |
| 2007/0213786 A1 | 9/2007 | Sackellares et al. |
| 2008/0269631 A1 | 10/2008 | Denison et al. |
| 2010/0121215 A1 | 5/2010 | Giftakis et al. |
| 2011/0245629 A1* | 10/2011 | Giftakis ............... A61B 5/0476 600/301 |

OTHER PUBLICATIONS

C. Stamoulis et al., "Modeling noninvasive neurostimulation in epilepsy as stochastic interference in brain networks," IEEE Transactions on Neural Systems and Rehabilitation Engineering, v. 21, n. 3, May 2013, p. 354-363, Institute of Electrical and Electronics Engineers.

G. Thomas et al.. "Critical review of the responsive neurostimulator system for epilepsy," Medical Devices: Evidence and Research, v. 2015, n. 8, Oct. 2015, p. 405-411, Dove Medical Press Limited.

G. Bergey et al., "Long-term treatment with responsive brain stimulation in adults with refractory partial seizures," Neurology, v. 84, n. 8, Feb. 24, 2015, p. 810-817, American Academy of Neurology.

S. Ramgopal et al., "Seizure detection, seizure prediction, and closed-loop warning systems in epilepsy," Epilepsy & Behavior, v. 37, Aug. 2014, p. 291-307, Elsevier Inc.

P. Mirowski et al., "Classification of Patterns of EEG Synchronization for Seizure Prediction." Clinical Neurophysiology, v. 120, n. 11, Nov. 2009, p. 1927-1940, Elsevier Ireland Ltd.

Neuropace, Inc., "Neuropace RNS System Clinical Summary," DN 1014918 Rev 2, Nov. 2014, p. 1-68, http://www.neuropace.com/manuals/ClinicalSummary.pdf.

J. Pineau et al., "Treating epilepsy via adaptive neurostimulation: A reinforcement learning approach." International Journal of Neural Systems, v. 19, n. 4, Aug. 2009, p. 227-240, World Scientific Publishing Company.

E. Nurse et al., "Decoding EEG and LFP signals using deep learning: heading TrueNorth," Proceedings of the ACM International Conference on Computing Frontiers (CF '16), May 2016, p. 259-266, Association for Computing Machinery.

C. Xiao et al., "An adaptive pattern learning framework to personalize online seizure prediction," IEEE Transactions on Big Data, v. PP, n. 99, Mar. 2017, p. 1-13, Institute of Electrical and Electronics Engineers.

K. Gadhoumi et al., "Seizure prediction for therapeutic devices: A review." Journal of Neuroscience Methods, v. 260, Feb. 15, 2016, p. 270-282, Elsevier B.V.

J. Williamson et al., "Seizure prediction using EEG spatiotemporal correlation structure." Epilepsy & Behavior, v. 25, n. 2, Oct. 2012, p. 230-238, Elsevier Inc.

J. Sirven, "Responsive Neurostimulation," Epilepsy Foundation, May 18, 2014, 3 pages, https://www.epilepsy.com/learn/treating-seizures-and-epilepsy/devices/responsive-neurostimulation.

* cited by examiner

*FIG. 3*

SEIZURE DETECTION, PREDICTION AND PREVENTION USING NEUROSTIMULATION TECHNOLOGY AND DEEP NEURAL NETWORK

BACKGROUND

The present invention relates to the electrical, electronic and computer arts, and, more particularly, to improvements in seizure detection, prediction and prevention using neurostimulation technology.

Neurostimulation is regarded a potential technique to prevent or treat seizures in epileptic patients. However, state-of-the-art neuromodulation technologies for epilepsy employ a one-fits-all technique which neither distinguishes between patients, nor between seizure types, durations and locations in the brain. Rather, current technologies apply the same neuromodulation signal ("white noise") non-stop to the same nerve (Vagus nerve) in all patients, with the hope that this will help to prevent seizures before they happen or counteract seizures as they happen. This is highly inefficient both, from a treatment efficacy/sensitivity standpoint and from an energy efficiency standpoint. Moreover, current technologies include pre-configured stimulation settings responsive to detection of seizures based on previously-identified brain patterns. Furthermore, conventional technologies are not only constrained to a set of pre-defined features, but also require a dedicated component for each pre-defined feature.

SUMMARY

A method for neuromodulation includes monitoring brain activity of a patient using one or more electrodes attached to the patient, and using a first machine learning model to predict whether a patient will have a seizure based on the monitored brain activity of the patient. The method also includes, responsive to the first machine learning model predicting that the patient will have a seizure, using a second machine learning model to determine a neuromodulation signal pattern for preventing the predicted seizure. The method further includes using a neurostimulator to apply the determined neuromodulation signal pattern to the patient. The method also includes, after applying the determined neuromodulation signal pattern to the patient, detecting whether the patient had the predicted seizure based on the monitored brain activity of the patient. The method further includes adjusting at least the second machine learning model based on whether the patient had the predicted seizure.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. An illustrative embodiment of the present invention advantageously provides a sophisticated neuromodulation strategy that can be accustomed to individual patients, individual seizure types/signals and the time-specific occurrence/onset of seizures. Furthermore, an illustrative embodiment advantageously predicts future seizures rather than merely detecting current seizures, thus allowing for intervention before a seizure happens. This intervention can be done in a self-learning, patient-specific, and adaptive way where relevant features are learned on a patient-by-patient basis. Notably, an illustrative embodiment does not require pre-defined features, much less a dedicated component for each pre-defined feature. Thus, an illustrative embodiment constitutes a major improvement over the state-of-the-art "white-noise", one-fits-all neurostimulation approach by allowing deployment of individually optimized stimulation patterns to specific patients and specific seizure types.

These and other features and advantages of the present invention will become apparent from the following detailed description of illustrative embodiments thereof, which is to be read in connection with the accompanying drawings.

DETAILED DESCRIPTION

An illustrative embodiment of the present invention advantageously provides a sophisticated neuromodulation strategy that can be accustomed to individual patients, individual seizure types/signals and the time-specific occurrence/onset of seizures. An illustrative embodiment advantageously predicts future seizures rather than merely detecting current seizures, thus allowing for intervention before a seizure happens. This intervention can be done in a self-learning, patient-specific, and adaptive way where relevant features are learned on a patient-by-patient basis.

An illustrative embodiment utilizes user-specific machine learning based classifier models for detecting and preventing seizures, including neural networks and deep learning to build a user-specific classifier model. An illustrative embodiment is not constrained to a set of pre-defined features, and does not require a dedicated component for each pre-defined feature. Rather, a deep neural network can automatically extract features that are tailored to each patient individually as part of the optimization and learning process, thus reducing the overhead of specialized components.

An illustrative embodiment of the invention provides enhanced seizure prevention by applying closed-loop neuromodulation in which a deep neural network model is used to determine the ideal signal pattern for neurostimulation. Thus, an illustrative embodiment of the present invention can advantageously apply a user-specific neuromodulation pattern to treat and/or prevent a specific type of seizure in an individual patient and only when needed (e.g. once a seizure has been predicted or is detected).

An illustrative embodiment of the present invention introduces such a novel neuromodulation scheme using a novel neuromodulation platform and system. Thus, an illustrative embodiment of the present invention includes a neuromodulation system for preventing and/or treating seizures in epileptic patients which uses a seizure prediction and seizure detection engine to continuously learn and optimize stimulation patterns from monitoring and analyzing an individual patients brain-activity. In an illustrative embodiment, this can be accomplished by real-time detection of specific patterns in the electroencephalography (EEG) signals of a patient which correspond to the onset of a seizure in the future (seizure prediction) and an actual seizure itself (seizure detection). An illustrative embodiment triggers a specific stimulation signal once a seizure is predicted and monitors success by determining whether a seizure subsequently happened (unsuccessful stimulation) or did not happen (successful stimulation). Memorizing the specific prediction/stimulation/detection patterns which belong to each such sequence of events can help to optimize a machine learning/deep learning engine which over time will be able to make smart choices as to which stimulation pattern works best for a specific prediction pattern in a specific patient.

Thus, an illustrative embodiment may include a system that adapts to patients on an individual basis given their specific seizure patterns and effective neural stimulation for seizure prevention. An illustrative embodiment updates stimulation patterns for seizure prevention based on their past efficacy for specific patients in an automated fashion. Specifically, an illustrative embodiment includes self-learning using information about successful or unsuccessful prevention attempts. An illustrative embodiment constitutes a major improvement over the state-of-the-art "white-noise", one-fits-all neurostimulation approach by allowing deployment of individually optimized stimulation patterns to specific patients and specific seizure types.

Figure 1:
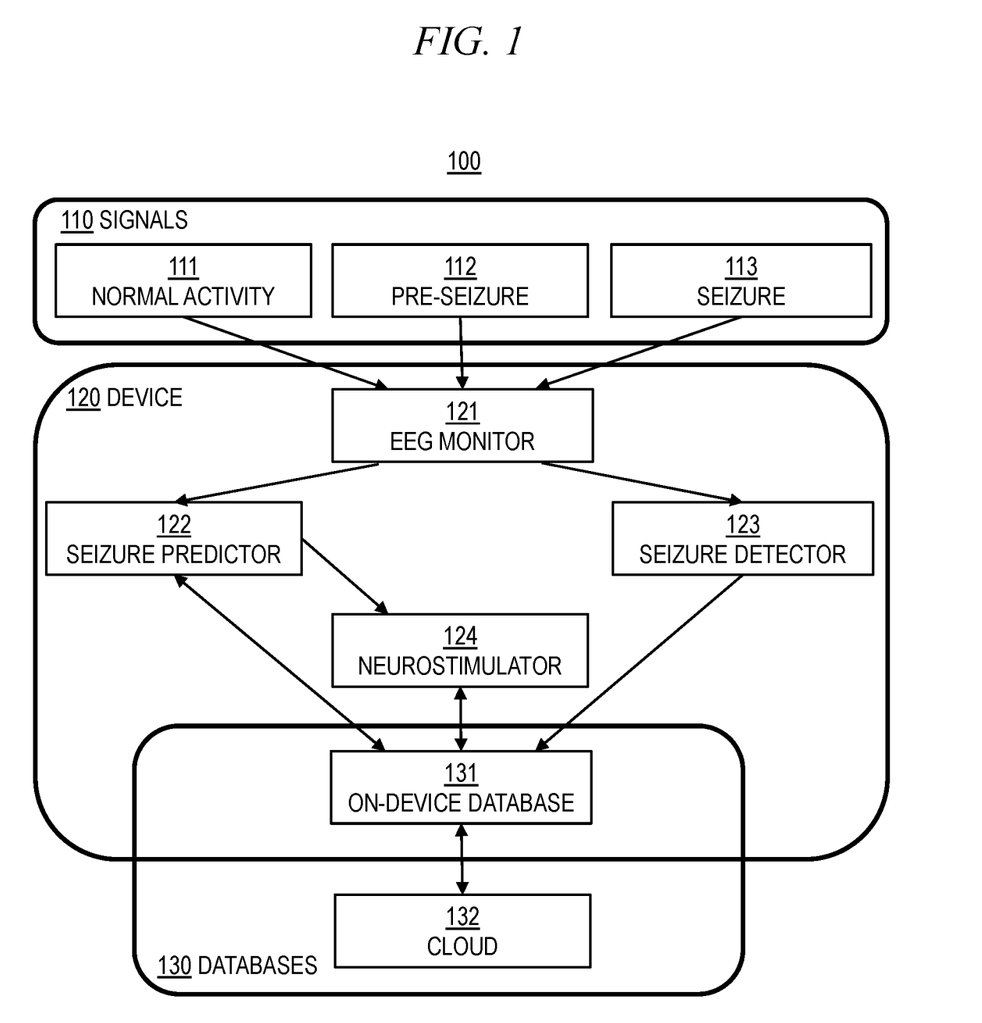
FIG. 1 shows an exemplary combined block/flow diagram showing an illustrative embodiment of the present invention.

FIG. 1 is an exemplary combined block/flow diagram 100 showing an illustrative embodiment of the present invention. Device 120 receives signals 110 comprising electroencephalograph (EEG) data of a patient. For example, signals 110 may be collected through electrodes which are attached to a human brain, e.g., implanted, sub-scalp, or above-scalp through an EEG cap. As will be further discussed below, signals 110 may indicate normal brain activity 111, pre-seizure activity 112 indicative of a future seizure, or seizure activity 113 indicative of a current seizure. Databases 130 may be internal to device 120 (e.g., on-device database 131) or external to device 120 (e.g., cloud 132).

Within device 120, EEG monitor 121 continuously monitors the EEG data in signals 110. EEG monitor 121 may convert signals 110 to a representation that allows neural network processing of the data, e.g., from electric time series to imagery data. As further discussed below, pre-seizure signals 112 and seizure signals 113 may be stored (e.g., by seizure predictor 122 and seizure detector 123) within databases 130 (e.g., on-device database 131) in both transformed and original data formats. EEG monitor 121 provides signals 110 (preferably in a converted format as discussed above) to seizure predictor 122, which determines whether signals 110 indicate pre-seizure activity 112, and to seizure detector 123, which determines whether signals 113 indicate seizure activity 113. If signals 110 are not determined by seizure predictor 122 to indicate neither pre-seizure activity 112 or by seizure predictor 123 to indicate seizure activity 113, then signals 110 are presumed to indicate normal brain activity 111.

Seizure predictor 122 and seizure detector 123 may comprise respective classifiers which use machine-learning/deep-learning techniques to recognize specific patterns (pre-seizure activity 112 and seizure activity 113, respectively) within brain signals (EEG data) 110. Seizure predictor 122 and seizure detector 123 may be initially calibrated with a certain number of samples of pre-seizure 112 and seizure 113 patterns (e.g., within databases 130). However, as discussed below, seizure predictor 122 and seizure detector 123 continuously learn and optimize patterns from monitoring and analyzing an individual patient's brain activity (e.g., using a deep neural network).

When seizure predictor 122 determines that signals 110 indicate pre-seizure activity 112, seizure predictor 122 stores pre-seizure signals 112 within databases 130 (e.g., on-device database 131), and also determines a future time at which seizure activity 113 is predicted to occur. When seizure predictor 122 determines that signals 110 indicate pre-seizure activity 112, seizure predictor 122 sends a prediction signal to neurostimulator 124. Neurostimulator 124, which may also comprise a classifier using machine-learning/deep-learning techniques, can tap into a repository of stimulation patterns (e.g., databases 130 including on-device database 131) which it can selectively choose and combine to generate custom stimulation signals. Neurostimulator 124 applies stimulation signal pulses to the brain through electrodes attached to the brain, which may be the same electrodes as or different electrodes than those used to collect signals 110. Neurostimulator 124 stores the applied stimulation signal pattern (e.g., in EEG format) within databases 130 (e.g., on-device database 131) in an entry corresponding to the aforementioned pre-seizure signals 112.

When seizure detector 123 determines that signals 110 do not indicate seizure activity 113 after seizure predictor 122 predicted seizure activity 113 would occur, then seizure detector 123 labels the database 130 entry, comprising the pre-seizure signals 112 and pattern applied by neurostimulator 124, as successful. However, if seizure detector 123 determines that signals 110 do indicate seizure activity 113 after seizure predictor 122 predicted seizure activity 113 would occur, then seizure detector 123 labels the entry in databases 130 (e.g., on-device database 131), comprising the pre-seizure signals 112 and pattern applied by neurostimulator 124, as unsuccessful and requiring adjustment of the neurostimulator 124. If seizure detector 123 determines that signals 110 indicate seizure activity 113 which was not predicted by seizure predictor 122, then seizure detector 123 stores the seizure signal 123 in databases 130 (e.g., on-device database 131) to indicate that seizure predictor 122 needs to be adjusted. Thus, an illustrative embodiment learns from occurrence of seizures, either after a prediction and despite stimulation (in which case the stimulation signal needs to be adjusted) or without an alert and without stimulation (in which case the prediction classifier needs to be adjusted).

The entries in databases 130 (e.g., on-device database 131) are continuously used to (re)train one or more neural network models (e.g., within seizure predictor 122, seizure detector 123, and/or neurostimulator 124) that predicts the most efficient stimulation signal from previous prediction/stimulation/detection instances using the successful/unsuccessful labels for training purposes. Thus, tracking which specific prediction/stimulation/detection patterns were successful or unsuccessful helps to optimize a machine learning/deep learning engine which over time will be able to make smarter choices as to which simulation pattern works best for a specific prediction pattern in a specific patient, thereby gradually optimizing both seizure prediction 122 and neurostimulation 124 activity for a specific patient.

As discussed above, seizure prediction 122 and seizure detection 123 signals may be stored in databases 130 (e.g., on-device database 131) in both transformed and original data formats, while neomodulation signals 124 may be stored in databases 130 (e.g., on-device database 131) in EEG format. After certain periods of time (e.g., once on-device database 131 is full, or seizure predictor 122, seizure detector 123, or neurostimulator 124 show decreasing performance), data can be ported from on-device database 131 into the cloud 132 for storage and further processing. Data can also be off-loaded from on-device database 131 into the cloud 132 if a model (e.g., 122, 123, or 124) needs to be retrained on data beyond that which can be stored on the device 120 (e.g., in on-device database 130). Also, updated models can be downloaded to the device 120 (e.g., on-device database 131) from the cloud 132. Similarly, pre-formed and/or customized stimulation patterns can be transferred to the device 120 (e.g., on-device database 131) from a cloud-based library 132.

Figure 2:
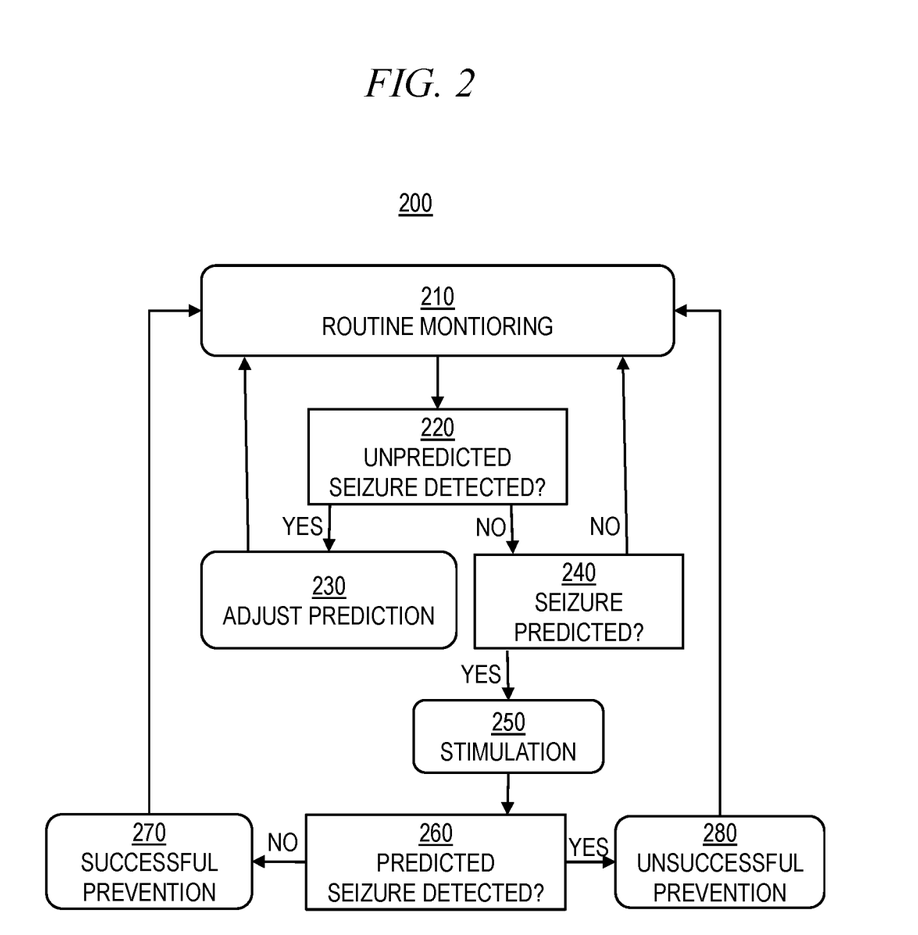
FIG. 2 is an exemplary flowchart showing an illustrative embodiment of the present invention.

FIG. 2 is an exemplary flowchart 200 showing an illustrative embodiment of the present invention. Step 210 includes routine monitoring (e.g., by monitor 121) of EEG data (e.g., signal 110). Step 220 determines whether a seizure is detected. In an illustrative embodiment discussed above with reference to FIG. 1, step 220 may include seizure detector 123 determining whether signal 110 indicates seizure activity 113. As further discussed below with reference to step 240 and 260, a seizure which is detected at step 220 would not have been predicted in step 240, and thus indicates that seizure predictor 112 requires adjustment 230 to increase its accuracy. After seizure predictor 112 is adjusted in step 230, the system resumes routine monitoring in step 210.

If no seizure is detected in step 220, then step 240 determines whether a seizure is predicted. In an illustrative discussed above with reference to FIG. 1, step 240 may include seizure predictor 122 determining whether signal 110 indicates pre-seizure activity 112. If step 240 determines that no seizure is detected or predicted (e.g., signal 110 indicates normal activity 111), then the system continues routine monitoring in step 210.

If step 240 determines that a seizure is predicted (e.g., signal 110 indicates pre-seizure activity 112), then the method proceeds to step 250, which includes application of a stimulation signal (e.g., by neurostimulator 124). At a certain period of time after application of stimulation signal in step 250 (e.g., at a time at which step 220 predicted the seizure would occur or after a predetermined period of time), step 260 determines whether a seizure is detected. In an illustrative embodiment discussed above with reference to FIG. 1, step 260 may include seizure detector 123 determining whether signal 110 indicates seizure activity 113.

If step 260 determines that no seizure is detected (e.g., signal 110 indicates normal activity 111), then the databases 130 are updated to indicate that the stimulation 250 successfully prevented the seizure in step 270. If step 260 determines that a seizure is detected (e.g., signal 110 indicates seizure activity 113), then the databases 130 are updated to indicate that the stimulation 240 was unsuccessful in step 280. After either step 270 or step 280, the system resumes routine monitoring in step 210. As discussed above, the successful 270 or unsuccessful 280 labels are used to gradually optimize both seizure prediction 220 and neurostimulation 240 for a specific patient. Moreover, an illustrative embodiment learns from occurrence of seizures, either in step 260 after a prediction (step 240) and despite stimulation (step 250) in which case the stimulation signal needs to be adjusted (step 280) or in step 220 without an alert and without stimulation in which case the prediction classifier needs to be adjusted (step 230).

Given the discussion thus far, it will be appreciated that, in general terms, an aspect of the invention comprises a method for neuromodulation including monitoring brain activity of a patient using one or more electrodes attached to the patient (e.g., 121 in FIG. 1 and/or 210 in FIG. 2), and using a first machine learning model to predict whether a patient will have a seizure based on the monitored brain activity of the patient (e.g., 122 in FIG. 1 and/or 240 in FIG. 2). The method also includes, responsive to the first machine learning model predicting that the patient will have a seizure, using a second machine learning model to determine a neuromodulation signal pattern for preventing the predicted seizure, and using a neurostimulator to apply the determined neuromodulation signal pattern to the patient (e.g., 124 in FIG. 1 and/or 250 in FIG. 2). The method further includes, after applying the determined neuromodulation signal pattern to the patient, detecting whether the patient had the predicted seizure based on the monitored brain activity of the patient (e.g., 123 in FIG. 1 and/or 260 in FIG. 2). The method also includes adjusting at least the second machine learning model based on whether the patient had the predicted seizure (e.g., 270 and/or 280 in FIG. 2).

One or more embodiments of the invention, or elements thereof, can be implemented, at least in part, in the form of an apparatus including a memory and at least one processor that is coupled to the memory and operative to perform exemplary method steps.

Figure 3:
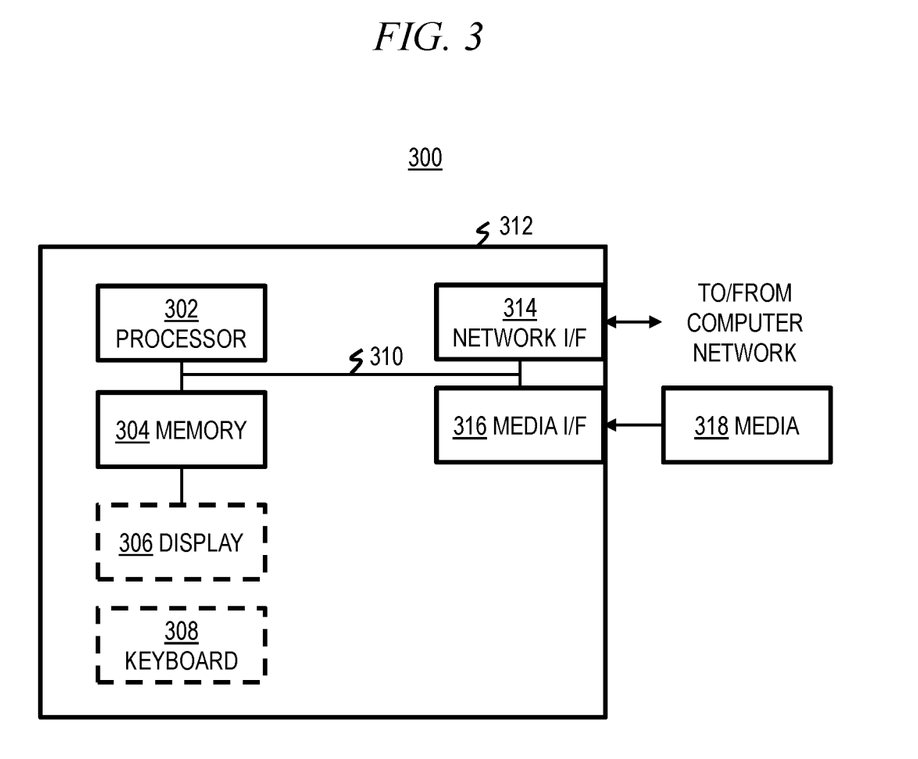
FIG. 3 shows a computer system that may be useful in implementing one or more aspects and/or elements of the invention.

One or more embodiments can make use of software running on a general purpose computer or workstation. With reference to FIG. 3, such an implementation might employ, for example, a processor 302, a memory 304, and an input/output interface formed, for example, by a display 306 and a keyboard 308. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit (for example, printer). The processor 302, memory 304, and input/output interface such as display 306 and keyboard 308 can be interconnected, for example, via bus 310 as part of a data processing unit 312. Suitable interconnections, for example via bus 310, can also be provided to a network interface 314, such as a network card, which can be provided to interface with a computer network, and to a media interface 316, such as a diskette or CD-ROM drive, which can be provided to interface with media 318.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 302 coupled directly or indirectly to memory elements 504 through a system bus 310. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 308, displays 306, pointing devices, and the like) can be coupled to the system either directly (such as via bus 310) or through intervening I/O controllers (omitted for clarity).

Network adapters such as network interface 314 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 312 as shown in FIG. 3) running a server program. It will be understood that such a physical server may or may not include a display and keyboard.

It should be noted that any of the methods described herein can include an additional step of providing a system comprising distinct software modules embodied on a computer readable storage medium; the modules can include, for example, any or all of the elements depicted in the block diagrams or other figures and/or described herein. The method steps can then be carried out using the distinct software modules and/or sub-modules of the system, as described above, executing on one or more hardware processors 302. Further, a computer program product can include a computer-readable storage medium with code adapted to be implemented to carry out one or more method steps described herein, including the provision of the system with the distinct software modules.

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for neuromodulation, the method comprising:
   monitoring brain activity of a patient using one or more electrodes attached to the patient;
   predicting, using a first machine learning model, whether a patient will have a seizure based on the monitored brain activity of the patient;
   responsive to the first machine learning model predicting that the patient will have a seizure, determining, using a second machine learning model, a neuromodulation signal pattern for preventing the predicted seizure;
   using a neurostimulator to apply the determined neuromodulation signal pattern to the patient;
   after applying the determined neuromodulation signal pattern to the patient, detecting whether the patient had the predicted seizure based on the monitored brain activity of the patient; and
   adjusting at least the second machine learning model based on whether the patient had the predicted seizure.

2. The method of claim 1, further comprising adjusting the first machine learning model responsive to detecting that the patient had a seizure not predicted by the first machine learning model.

3. The method of claim 1, wherein adjusting at least the second machine learning model based on whether the patient had the predicted seizure comprises:
   if the patient did not have the predicted seizure, determining that the determined neuromodulation signal pattern was successful in preventing the predicted seizure; and
   if the patient did have the predicted seizure, determining that the determined neuromodulation signal pattern was unsuccessful in preventing the predicted seizure.

4. The method of claim 1, wherein the neuromodulation signal pattern determined by the second machine learning model is specific to the patient.

5. The method of claim 1, wherein the first machine learning model predicts whether the patient will have a seizure by determining whether the monitored brain activity of the patient matches at least one pre-seizure pattern.

6. The method of claim 5, wherein the pre-seizure pattern matched by the first machine learning model is specific to the patient.

7. The method of claim 5, wherein the neuromodulation signal pattern determined by the second machine learning model is specific to the pre-seizure pattern matched by the first machine learning model.

8. The method of claim 1, wherein at least the second machine learning model comprises a deep neural network.

9. The method of claim 1, wherein at least the first machine learning model comprises a deep neural network.

10. The method of claim 1, wherein detecting whether the patient had the predicted seizure comprises detecting, using at least a third machine learning model, whether the patient had the predicted seizure based on the monitored brain activity of the patient.

11. The method of claim 1, wherein determining the neuromodulation signal pattern using the second machine learning model comprises choosing and combining from a local repository of potential neuromodulation signal patterns.

12. The method of claim 11, further comprising transferring one or more potential neuromodulation signals from a remote storage into the local repository.

13. The method of claim 1, further comprising:
   transmitting the second machine learning model to a remote storage for updating; and
   receiving an updated second machine learning model from the remote storage.

14. The method of claim 1, further comprising:
transmitting the first machine learning model to a remote storage for updating; and
receiving an updated first machine learning model from the remote storage.

15. An apparatus for neuromodulation, comprising:
a memory; and
at least one processor coupled to the memory, the processor being operative:
- to monitor brain activity of a patient using one or more electrodes attached to the patient;
- to predict, using a first machine learning model, whether a patient will have a seizure based on the monitored brain activity of the patient;
- responsive to the first machine learning model predicting that the patient will have a seizure, to determine, using a second machine learning model, a neuromodulation signal pattern for preventing the predicted seizure;
- to use a neurostimulator to apply the determined neuromodulation signal pattern to the patient;
- after applying the determined neuromodulation signal pattern to the patient, to detect whether the patient had the predicted seizure based on the monitored brain activity of the patient; and
- to adjust at least the second machine learning model based on whether the patient had the predicted seizure.

16. The apparatus of claim 15, wherein determining the neuromodulation signal pattern using the second machine learning model comprises choosing and combining from a repository of potential neuromodulation signal patterns stored within the memory of the apparatus.

17. The apparatus of claim 16, further comprising transferring one or more potential neuromodulation signals from a remote storage into the memory of the device.

18. The apparatus of claim 15, wherein the processor is further operative:
- to transmit the second machine learning model to a remote storage for updating; and
- to receive an updated second machine learning model from the remote storage.

19. The apparatus of claim 15, wherein the processor is further operative:
- to transmit the first machine learning model to a remote storage for updating; and
- to receive an updated first machine learning model from the remote storage.

20. A computer program product comprising a non-transitory machine-readable storage medium having machine-readable program code embodied therewith, said machine-readable program code comprising machine-readable program code configured:
- to monitor brain activity of a patient using one or more electrodes attached to the patient;
- to predict, using a first machine learning model, whether a patient will have a seizure based on the monitored brain activity of the patient;
- responsive to the first machine learning model predicting that the patient will have a seizure, to determine, using a second machine learning model, a neuromodulation signal pattern for preventing the predicted seizure;
- to use a neurostimulator to apply the determined neuromodulation signal pattern to the patient;
- after applying the determined neuromodulation signal pattern to the patient, to detect whether the patient had the predicted seizure based on the monitored brain activity of the patient; and
- to adjust at least the second machine learning model based on whether the patient had the predicted seizure.

* * * * *